United States Patent [19]
Goel et al.

[11] Patent Number: 5,900,394
[45] Date of Patent: * May 4, 1999

[54] DETERGENT COMPOSITIONS FOR ENHANCED DELIVERY OF FUNCTIONAL INGREDIENTS

[75] Inventors: Satish Kumar Goel; Devadatta Shivaji Sankholkar, both of Mumbai, India

[73] Assignee: Lever Brothers Company, New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 08/833,561

[22] Filed: Apr. 7, 1997

[30] Foreign Application Priority Data

Apr. 10, 1996 [IN] India ............................................ 198/96
May 25, 1996 [GB] United Kingdom .................... 9610966

[51] Int. Cl.⁶ .............................. A61K 7/50; C11D 17/00
[52] U.S. Cl. .......................... 510/141; 510/146; 510/151; 510/447; 510/471
[58] Field of Search ..................................... 510/141, 146, 510/151, 447, 471

[56] References Cited

U.S. PATENT DOCUMENTS

| | | | |
|---|---|---|---|
| 3,723,325 | 3/1973 | Parran | 252/106 |
| 4,061,602 | 12/1977 | Oberstar et al. | 252/547 |
| 4,634,564 | 1/1987 | Kerslake | 264/75 |
| 4,704,224 | 11/1987 | Saud | 252/132 |
| 4,820,447 | 4/1989 | Medcalf, Jr. et al | 252/117 |
| 5,064,555 | 11/1991 | Medcalf, Jr. et al. | 252/117 |
| 5,296,159 | 3/1994 | Wilson et al. | 252/117 |
| 5,547,602 | 8/1996 | Schuler | 510/151 |
| 5,629,276 | 5/1997 | Subramanyam et al. | 510/141 |
| 5,683,972 | 11/1997 | Zocchi | 510/471 |

FOREIGN PATENT DOCUMENTS

| | | |
|---|---|---|
| 0 93 601 | 9/1983 | European Pat. Off. . |
| 0 311 343 | 12/1989 | European Pat. Off. . |
| WO 94/03152 | 2/1994 | WIPO . |
| WO 95/22311 | 8/1995 | WIPO . |

*Primary Examiner*—Jerry D. Johnson
*Attorney, Agent, or Firm*—Rimma Mitelman

[57] ABSTRACT

A novel system for enhanced delivery of functional ingredients, particularly of benefit agents used in detergent/soap compositions, comprises a synergistic oil-in-water type emulsion with an internal oil phase of said benefit agent and an external water phase thickened with cationic polymer.

4 Claims, No Drawings

DETERGENT COMPOSITIONS FOR ENHANCED DELIVERY OF FUNCTIONAL INGREDIENTS

The present invention relates to a novel system for enhanced delivery of functional ingredients for use preferably in soap/detergent formulations. In particular, the invention is directed to enhancing the deposition of benefit agents such as organic sunscreens, emollients, humectants, antimicrobial agents and insect repellants onto skin, hair or other substrates from soap/detergent based washing compositions.

It is presently known in the art to use natural polysaccharide type polymers modified by adding cationic groups (for example, Jaguar, a registered trade name of Rhone Poulenc for cationic derivative of guar gum) as well as synthetic cationic polymers in washing formulations for providing better skin and hair feel. There are several patents describing their use as conditioners in liquid or gel type products. For instance, U.S. Pat. No. 4,061,602 (American Cyanamide Co.) describes them as ingredients which add substance to hair and skin without building up after successive applications. EP 311,343 (P&G) suggests their use in solid soap bars for giving benefits related to mildness, scum-control and lather. The method of incorporation of Jaguar into the final product in these cases is by way of adding the Jaguar powder directly with the other ingredients of the product and mixing it thoroughly. U.S. Pat. No. 4,704,224 (P&G) describes a better method of incorporating Jaguar in soap bars which is by way of preparing a small adjunct where Jaguar is dispersed in coconut fatty acid and neutralized separately before adding it to the rest of the soap. U.S. Pat. No. 803,742 (P&G) describes yet another method involving hydration of Jaguar with water prior to mixing it uniformly into the soap bars to give improved feel and mildness effect.

U.S. Pat. No. 3,723,325 (P&G), South Africa 6805,954 (P&G), EP 93,601 (Unilever), WO 9522311 (Unilever), WO 93EP2072 (Unilever) and GB 8212687 (Unilever) all describe the use of Jaguar and cationic polymers to enhance deposition of particulate solid benefit agents onto skin from washing compositions (mainly soap bars). WO 9403152 (Unilever) describes a similar application however, for deposition of silicone oil instead of solid particles. However, irrespective of the intended benefit agent used for delivery, all the above discussed known art methods are directed to the incorporation of Jaguar/cationic polymer by simply mixing it as powder in the formulation.

It is thus the basic objective of the present invention to provide for a novel system of enhanced delivery of functional ingredients for use in particular in soap/detergent bar formulations.

A further object of the present invention is to provide for suitable method(s) of incorporation of the system for enhanced delivery of the functional ingredient in soap/detergent bar formulations.

Yet a further object of the present invention is to provide synergistic soap/detergent bar formulations which would provide for improved functional ingredient delivery onto substrates on which they are applied thereby obtaining maximum effective value of the benefit agents used in such bar formulations.

Another object of the present invention is directed to provide for a soap/detergent bar formulations with enhanced benefit agent depositing properties in a form which would be convenient for the user.

Thus, according to one aspect, the present invention provides a system for enhanced delivery of benefit agent for use in detergent/soap bar formulations, the system comprising a synergistic oil-in-water type emulsion with an internal oil phase of said benefit agent and an external water phase thickened with cationic polymer.

The functional ingredient/benefit agent and the cationic polymer, when incorporated as said oil-in-water type emulsion in soaps/detergent based washing compositions, provide for enhanced deposition of the benefit agent such as organic sunscreen, Parsol MCX (a registered trade name of Givaudan Roure and chemically 2-ethyl-hexyl-methoxy cinnamate), Parsol 1789 (chemically known as butyl methoxy benzoylmethane) onto skin, hair and other substrate from soaps or detergent based washing compositions.

Suitable benefit agents which can be used in such emulsion system includes organic sun screen, emollients, humectants, antimicrobial agents and insect repellants.

The external water phase in the emulsion system is thickened by the addition of cationic polymers which includes JAGUAR (a tradename for cationic guar gum which is 2-hydroxy-3-(trimethylammonio)propyl guar gum). The cationic polymer can be used in the range of 0.25 to 5% and preferably 1–2% based on the external water phase.

Preferably the oil-in-water emulsion system typically has an internal oil phase of more than 30% and more preferably greater than 50% to give higher concentration of deposition of said benefit agent.

The oil-in-water type of emulsion system of the invention described above can be obtained as follows:

a. Providing a solution of the cationic polymer in water;
b. Mixing a suitable emulsifier preferably having HLB~4–10 with the selected benefit agent/functional ingredient.
c. The mixture in (b) is next subjected to high shear mixing preferably in a Silverson mixer while the solution in (a) is added slowly to it, to thereby obtain the benefit agent as oil-in-water type emulsion system of the invention.

According to another aspect of the present invention is provided a detergent/soap/washing composition formulations having improved functional ingredient depositing characteristic by way of incorporation of the benefit agent in the form of said oil-in-water type emulsion system in such bar formulations.

In accordance with such aspect of the invention the benefit agent in the form of the oil-in-water emulsion system is incorporated in the basic soap/detergent composition formulation which is selected from:

anionic surfactants such as sodium or potassium salts of fatty acids of varying chain lengths (soaps), sodium linear alkyl benzene sulphonate, alpha olefin sulphonate, sodium lauryl ether sulphate and primary alkyl sulphates in the range of about 10 to 80%;

non-ionic surfactants such as alkyl alcohol ethoxylates in the range of about 2 to 20%; and other surfactants such as cationic betaines in the range of about 2 to 10%;

particulate minerals such as clays, talc and calcite in the range of about 0 to 40%;

soda ash in the range of about 0 to 10%;

builders such as sodium phosphates or zeolites in the range of about 0 to 20%;

binders such as alkaline sodium silicate in the range of about 0 to 5%; or other optional minor ingradients such as perfumes, bleaches, optical brighteners and enzymes; or mixtures thereof.

The benefit agents used include organic sunscreens, emollients, humectants, antimicrobial agents and insect repellants is in the range of about 0.1 to 5%. The benefit agent in the range of 0.1–5% is provided in the form of the oil-in-water emulsion in said bar formulation to achieve improved functional ingredient deposition characteristics in such bar formulations.

According to yet further aspect of the present invention the same is directed to providing for suitable methods of incorporation of the benefit agent/functional ingredients in the form of the oil-in-water type emulsion system of the invention in product bar formulation such as soaps/detergent bars/washing compositions to obtain effective deposition of the functional ingredients/benefit agent onto substrates on which such products (bar formulations) are applied.

In particular, the invention thus further proposes incorporation of the oil-in-water type emulsion system containing the benefit agent into the final product in the form of any one or more of the following:

i) discrete domains of the emulsion (equivalently of the benefit agent since the emulsion has high concentration of the benefit agent);

ii) adding of the benefit agent in the form of the emulsion as stripes on the extruded soap bars preferably by injection facility on the plodder; and iii) filing in the benefit agent in the form of the emulsion in a separate zone of a divided tube dispenser such that the benefit agent in the form of said emulsion flows out as stripes adhering to the main ribbon of a gel product as the tube is squeezed.

The nature of the present invention, its objectives and advantages will be further apparent from the ensuing description made with relation to non-limiting exemplary modes of obtaining the benefit agent in the form of oil-in-water type emulsion system of the invention and its incorporation in exemplary bar formulations as discussed hereunder.

EXAMPLE 1

(A) Preparation of emulsion

In this example, 1% solution of Jaguar in water was first prepared using an overhead stirrer. An emulsifier (Tween 60) having HLB~10 was mixed with a combination of benefit agents comprising Parsol MCX with Parsol 1789 (80:20 proportions).

This mixture of sunscreen with the emulsifier was next subjected to high shear mixing using a Silverson mixer while the Jaguar solution was added slowly to it. Mixing was continued for about 5 minutes after complete addition of Jaguar solution to homogenise the emulsion. The composition of the emulsion was Parsol mix: 55.6%, Tween 60: 7.5%, and 1% Jaguar solution: 36.9%.

(B) Incorporation of oil-in-water emulsion of (A) above, into the product—by way of incorporation of the benefit agent in the form of speckled bars The emulsion system thus obtained in step (A) above was incorporated at 1.8% into a soap base comprising 30% coconut oil fatty acid salt, the balance being the salts of distilled fatty acids derived from a mixture of oils (eg. rice bran/palm) of moisture content 13%. The emulsion was incorporated into the product by very light blending of the emulsion with soap base in a ribbon mixer for just less than a minute followed by compaction of mix under pressure.

The level of incorporation of emulsion was 3.6% and the average level of Parsol mix in the product was 2%.

EXAMPLE II (A) Preparation of the emulsion

In this example, 1% solution of Jaguar in water was first prepared using an overhead stirrer. An emulsifier (Tween 60) having HLB~10 was mixed with a combination of benefit agents comprising Parsol MCX with Parsol 1789 (80:20 proportions).

This mixture of sunscreen with the emulsifier was next subjected to high shear mixing using a Silverson mixer while the Jaguar solution was added slowly to it. Mixing was continued for about 5 minutes after complete addition of Jaguar solution homogenise the emulsion. The composition of the emulsion was the same as in (A) of Example I.

(B) Incorporation of oil-in-water emulsion of (A) above into the product—by way of incorporation of the benefit agent in the form of striped bars The oil-in-water type emulsion system of (A) above was next incorporated into the product bar formulation similar to that of Example I in the form of stripes by die injection technique so that the average level of Parsol mix in the product was 2.5%.

EXAMPLE III

Control bar formulation

In this example, a control bar formulation was made from the soap base containing 30% coconut oil fatty acid salt, the balance being the salts of distilled fatty acids derived from a mixture of oils (e.g., rice bran/palm) of moisture content of 13% without incorporation of any Parsol mix.

The deposition of Parsol onto the skin in use of the bar formulations of the invention (Examples I and II) and the control bar formulation (Example III) was estimated.

The estimation of Parsol deposition was carried out on 9 panelists following the under-mentioned procedure:

Twenty 'to and fro' rubs of the bar were given on prewashed inner forearm, the product was rubbed with the other hand to generate lather for 10 seconds, followed by rinsing, dab drying, and extraction with 400 micro liters of alcohol from 9 $cm^2$. The results of a comparative study of deposition from bar formulations according to Examples I to II vis-a-vis the control bar formulation III are provided hereunder in Tables I and II.

Comparative study of Parsol deposition from bar formulation according to Example I vis-a-vis Example III (control) is provided hereunder Table I.

TABLE I

| Deposition of Parsol (Micrograms on 9 $cm^2$)* | | |
|---|---|---|
| Example I | Example III | Difference |
| 3.07 | 2.30 | 0.77+ |

*Data are average of 9 values.
+Significant at 95% confidence.

The above Table I shows that with 95% statistical confidence Parsol MCX is deposited from the bar formulation (Example I) of the invention onto the skin to the extent of 0.77±0.27 micrograms on 9 $cm^2$ (ie., at least 0.50 microgram/9 $cm^2$) Comparative study of Parsol deposition from bar formulation according to Example II vis-a-vis Example III (control) is provided hereunder in Table II.

TABLE II

Deposition of Parsol (Micrograms on 9 cm²)*

| Example II | Example III | Difference |
|---|---|---|
| 2.94 | 1.72 | 1.22⁺ |

*Data are average of 9 values.
⁺Significant at 95% confidence.

The above Table II shows that with 95% confidence Parsol MCX is deposited from the bar formulations (Example II) of the invention onto the skin to the extent of $1.22 \pm 0.38$ micrograms on 9 cm² (i.e., at least 0.84 microgram on 9 cm²).

It is thus evident from the above results in Tables I and II that Parsol in water emulsions of satisfactory stability could be obtained wherein the aqueous phase is stabilized by cationic polymer such as Jaguar and that these emulsions could be used to generate macro domains of the benefit agent such as Parsol in soap/detergent bar formulations. Importantly, a comparative study of Tables I and II further reveal that at 2% or more Parsol mix (80:20) a consistent and significant enhanced level of deposition on skin is achieved using the bar formulations (Example I and II) of the invention as compared to control formulation (Example III).

Product Assessment

The product assessment of the bars having bar formulations according to Example I obtained by the process of the invention were next assessed vis-a-vis the control bar formulations according to Example III. The results are reproduced hereunder in Table III.

TABLE III

| Product attribute | Example III Control | Example I (2% Parsol) | C.D. |
|---|---|---|---|
| Lather, soft | 240 | 245 | 12.1 |
| Lather, hard | 193 | 191 | 14 |
| % Wear | 35.1 | 35.9 | 2.2 |
| Mush | 8.3 | 9.2 | 3.1 |

The above Table III clearly indicates that the product attributes of bar formulations according to Example I of the invention are comparable to the control bar formulation Example III.

It is thus clearly evident from the above disclosure that in the use of benefit agent in the form of oil-in-water emulsion system according to the invention in soap/detergent bar products in the manner proposed above, the deposition of benefit agent onto the skin/other substrate is significantly enhanced. Further such enhanced deposition of the benefit agent can be achieved following the process of incorporation of the same in detergent/soap bar formulations according to the invention even at very low levels of use of cationic polymer in combination with the benefit agent by way of the novel oil-in-water emulsion system of the invention.

We claim:

1. A detergent soap bar composition comprising discrete domains of an oil-in-water emulsion, the emulsion comprising:

(a) an internal oil phase comprising the benefit agent selected from the group consisting of an organic sun screen, an emollient, a humectant, an antimicrobial agent and an insect repellent, wherein the internal oil phase is present in an amount greater than 50% by weight of the emulsion; and (b) an external water phase thickened with a cationic polymer present in an amount of 0.25 to 5.0%, based upon the external water phase.

2. A composition as claimed in claim 1, further comprising any of the following:

anionic surfactants selected from the group consisting of sodium or potassium salts of fatty acids of varying chain lengths, sodium linear alkyl benzene sulphonate, alpha olefin sulphonate, sodium lauryl ether sulphate and primary alkyl sulphates in the range of about 10 to 80%;

non-ionic surfactants selected from the group consisting of alkyl alcohol ethoxylates in the range of about 2 to 20%;

cationic betaine surfactants in the range of about 2 to 10%;

particulate minerals selected from the group consisting of clays, talc and calcite in the range of about 0 to 40%;

soda ash in the range of about 0 to 10%;

builders selected from the group consisting of sodium phosphates and zeolites in the range of about 0 to 20%;

binders selected from the group consisting of alkaline sodium silicates in the range of about 0 to 5%; or other optional minor ingredients selected from the group consisting of perfumes, bleaches, optical brighteners and enzymes; or mixtures thereof.

3. The bar composition as claimed in claim 1 wherein the amount of the cationic polymer is from 1 to 2%.

4. A method of producing a detergent soap bar composition, the method comprising:

(a) providing a solution of the cationic polymer in water to obtain the external water phase, the polymer being present in an amount of 0.25% to 5.0%, based upon the external water phase;

(b) mixing an emulsifier having HLB 4-10 with a benefit agent to obtain the internal oil phase;

(c) subjecting the mixture resulting from step (b) to high shear mixing while adding the solution of step (a) wherein the mixture from step (b) is present in an amount greater than 50%;

(d) forming discrete domains of the emulsion resulting from step (c) in the bar composition by incorporating the emulsion into soap base.

* * * * *